United States Patent [19]

King et al.

[11] Patent Number: 4,946,966
[45] Date of Patent: Aug. 7, 1990

[54] 1-METHYLINDAZOLE-3-CARBOXYLIC ACID PROCESS

[75] Inventors: Francis D. King; Thomas W. Ramsay, both of Harlow, England

[73] Assignee: Beecham Group P.L.C., Brentford, England

[21] Appl. No.: 287,109

[22] Filed: Dec. 20, 1988

[30] Foreign Application Priority Data

Dec. 22, 1987 [GB] United Kingdom ............... 8729801

[51] Int. Cl.$^5$ .......................................... C07D 231/56
[52] U.S. Cl. .................................................. 548/372
[58] Field of Search ......................................... 548/372

[56] References Cited

U.S. PATENT DOCUMENTS 3,736,332  5/1973  Butula ................................. 548/372

OTHER PUBLICATIONS

Wiley, *Pyrazoles, Pyrazolines, Pyrazolidines, Indazoles and Condensed Rings*, (1967), pp. 309–313.
Auwers et al., *Chemical Abstracts*, vol. 14 (1920), pp. 3662–3663.
V. Rousseau et al., "Structure and Ultraviolet Absorption Spectra of Indazole, 3-Substituted Indazole and Some of Their Derivatives", *Journal of the American Chemical Society*, 72, pp. 3047–3051 (1950).

*Primary Examiner*—Robert W. Ramsuer
*Attorney, Agent, or Firm*—James F. Haley, Jr.; Leon R. Yankwich; Kenneth H. Sonnenfeld

[57] ABSTRACT

A process for the preparation of a compound of formula (I):

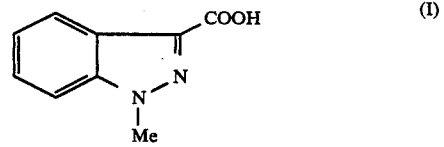

which comprises the reactive of a methylating agent with a compound of formula (IV):

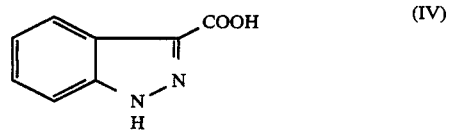

in a polar solvent in which is dissolved an alkali metal alkoxide, in an inert atmosphere.

7 Claims, No Drawings

1-METHYLINDAZOLE-3-CARBOXYLIC ACID PROCESS

This invention relates to a process for the preparation of a compound useful as an intermediate in the preparation of pharmaceutical compounds.

The compound 1-methylindazole-3-carboxylic acid of formula (I):

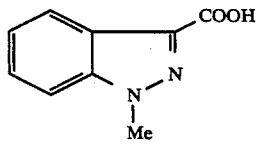

is a useful intermediate in the preparation of compounds which are 1-methylindazolyl azabicyclo esters or amides, such as those disclosed in EP-A-200444 (Beecham Group p.l.c.), in particular, the compound N-(endo-9-methyl-9-azabicyclo[3.3.1]non-3-yl) -1- methylindazole-3-carboxamide and its hydrochloride salt, designated BRL 43694A.

The literature reference for the preparation of this compound, K.V. Auwers and R. Deresser: Chem. Ber. 1919 52, 1340, involves methylation of the compound of formula (II):

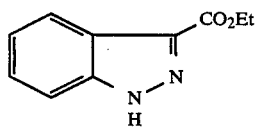

which gives a roughly equal mixture of two products containing the methyl group at either the 1- or 2-position. The mixture of products then has to be separated by chromatographic methods and then the required 1-methyl ester hydrolysed to give the compound of formula (I). This is a clearly undesirable route as it results in low yields and involves expensive and time consuming separation of a mixture of products.

An alternative process involving methylation of the compound of formula (III):

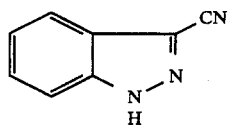

is described by V. Rousseau and H.G. Lindwall JACS 1950, 72 3047, but this also results in a mixture of isomers and a subsequent hydrolysis step.

A high yielding, one stage process has now been discovered, which avoids the need for separation of a mixture of products.

Accordingly, the present invention provides a process for the preparation of a compound of formula (I):

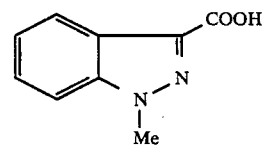

which comprises the reaction of a methylating agent with a compound of formula (IV):

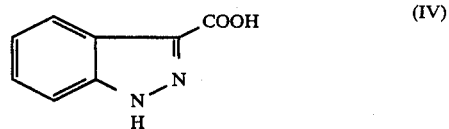

in a polar solvent in which is dissolved an alkali metal alkoxide, in an inert atmosphere.

Suitable examples of the methylating agent include dimethylsulphate and iodomethane or another compound of formula $CH_3X$ wherein X is a leaving group, such as mesylate or tosylate. About one mole equivalent is usually used.

Suitable examples of solvents include lower alkanols such as ethanol, n- or iso-propanol n-, iso-, sec- and tert-butanol; or dimethylformamide or dimethylsulphoxide. Preferably, the solvent is iso-propanol (2-propanol).

The alkali metal may suitably be lithium, sodium or potassium, preferably sodium, the alkoxide usually being formed in situ by reaction of alkali metal with a lower alkanol solvent. Usually, two mole equivalents of alkali metal are used.

Owing to the reactivity of alkali metals in an atmosphere containing oxygen, the reaction is carried out in an inert atmosphere, usually under nitrogen.

The reaction is normally carried out under reflux.

The reaction occurs by initial formation of the N- and COO— dianion of the compound of formula (IV), by the alkali metal. The dianion is then converted to the compound of formula (I), by the methylating agent.

Preferably the initial reaction to form the dianion is allowed to proceed for 1–2 hours, usually around 1½ hours, when sodium is used, and the subsequent reaction time with the methylating agent will depend on its reactivity, but around 3 hours is usually adequate when dimethylsulphate or iodomethane is used.

The above described process is suitable for large scale production of the compound of formula (I).

The following example illustrates the invention.

EXAMPLE: PREPARATION OF 1-METHYLINDAZOLE-3-CARBOXYLIC ACID

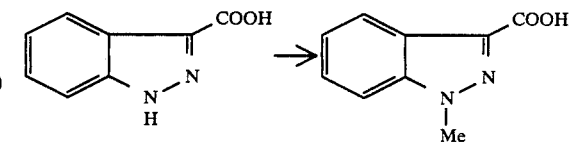

Sodium metal (0.2 Mol.) is added in portions to 2-propanol (100ml) at reflux under a nitrogen atmosphere. When all the sodium has dissolved, indazole-3-carboxylic acid (0.1 Mol.) is added to the stirred solution and the reflux is continued for a further 1½ hrs. A solution of dimethylsulphate or iodomethane (0.1 Mol.) in 2-propanol (20ml) is then added over 1 hr and the reflux is continued for a further 3 hrs. The suspension is allowed to cool overnight. Water is then added and the 2-propanol removed under reduced pressure. The resulting solution is washed with ethyl acetate. Diethyl ether or 4-methyl-2-pentanone is added to the aqueous solution and the mixture is stirred vigorously whilst a slight excess of hydrocholoric acid is added. The solid product is collected by filtration, washed with water, and dried. (Yield: 85–90%).

We claim:

1. A process for the preparation of a compound of formula (I):

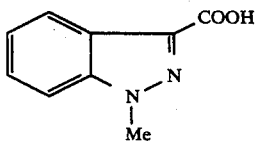

which comprises the reaction of a methylating agent with a compound of formula (IV):

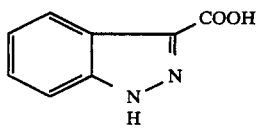

in a non-aqueous polar solvent in which is dissolved an alkali metal alkoxide, in an inert atmosphere.

2. A process according to claim 1 wherein the methylating agent is dimethylsulphate or iodomethane.

3. A process according to claim 1 wherein the non-aqueous polar solvent is a lower alkanol.

4. A process according to claim 1 wherein the solvent is 2-propanol.

5. A process according to claim 3 or 4 wherein the alkali metal alkoxide is formed in situ by reaction of alkali metal with the lower alkanol solvent.

6. A process according to claim 5 wherein the alkali metal is sodium.

7. A process for the preparation of a compound of formula (I)

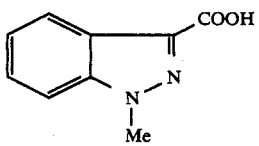

which process comprises the reaction of a methylating agent selected form the group consisting of iodomethane and dimethyl sulfate with a compound of formula (IV)

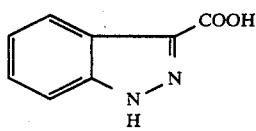

in a non-aqueous polar solvent consisting of a lower alkanol in which is dissolved sodium alkoxide in an inert atmosphere under reflux conditions.

* * * * *